United States Patent
Simari et al.

(10) Patent No.: US 8,637,462 B2
(45) Date of Patent: Jan. 28, 2014

(54) METHODS FOR REDUCING PLATELET COUNTS AND/OR PLATELET ADHESION BY ADMINISTERING A GC-B RECEPTOR AGONIST

(75) Inventors: Robert D. Simari, Rochester, MN (US); Sinny Delacroix, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/360,039

(22) Filed: Jan. 27, 2012

(65) Prior Publication Data

US 2012/0220527 A1 Aug. 30, 2012

Related U.S. Application Data

(60) Provisional application No. 61/437,432, filed on Jan. 28, 2011.

(51) Int. Cl.
*A61K 38/36* (2006.01)
*C07K 14/575* (2006.01)
*A61K 38/16* (2006.01)

(52) U.S. Cl.
USPC .......................... 514/13.8; 514/12.4; 530/326

(58) Field of Classification Search
None
See application file for complete search history.

(56) References Cited

U.S. PATENT DOCUMENTS

2004/0087539 A1 5/2004 Du

OTHER PUBLICATIONS

Scotland et al, 2005. PNAS. 102(40): 14452-14457.*
Komatsu et al, 2002. J Bone Miner Metab. 20: 331-336.*
Bougie et al., "Drug-dependent clearance of human platelets in the NOD/scid mouse by antibodies from patients with drug-induced immune thrombocytopenia," *Blood*, Oct. 2010, 116(16):3033-3038.
Boylan et al., "Activation-independent, antibody-mediated removal of GPVI from circulating human platelets: development of a novel NOD/SCID mouse model to evaluate the in vivo effectiveness of anti-human platelet agents," *Blood*, Mar. 2006, 108(3):908-914.
Burstein, "Megakaryocytopoiesis in culture: modulation by cholinergic mechanisms," *J Cell Physiol.*, May 1980, 103(2):201-208.
Dai et al., "Formation of platelets from cord blood CD34+ cells-derived megakaryocytes induced by 5-nitrosoglutathione," *Acta Physiologica Sinica*, Oct. 2006, 58(5):490-493.
Delacroix et al., "NPR-B Expression in Megakaryocytes and Platelets," American Society of Hematology [online], 2010, [retrieved on May 10, 2013]. Retrieved from the Internet: < URL: https://ash.confex.com/ash/2010/webprogram/Paper33427.html>., 1 page.
GenBank Accession No. NP_077720.1; GI No. 13249346, "C-type natriuretic peptide precursor [*Homo sapiens*]," 2 pages, Dec. 2009.
Huang et al., "STAT1 promotes megakaryopoiesis downstream of GATA-1 in mice," *J. Clin. Invest.*, Dec. 2007, 117(12):3890-3899.
Kobsar et al., "Cyclic nucleotide-regulated proliferation and differentiation vary in human hematopoietic progenitor cells derived from healthy persons, tumor patients, and chronic myelocytic leukemia patients," *Stem Cells Dev.*, Feb. 2008, 17(1):81-91.
Komatsu et al., "Significance of C-type natriuretic peptide (CNP) in endochondral ossification: analysis of CNP knockout mice," *J. Bone Miner Metab.*, 2002, 20(6):331-336.
Lisy et al., "Design, synthesis, and actions of a novel chimeric natriuretic peptide: CD-NP," *J. Am. Coll. Cardiol.*, Jul. 2008, 52(1):60-68.
Moraes et al., "Platelet endothelial cell adhesion molecule-1 regulates collagen-stimulated platelet function by modulating the association of phosphatidylinositol 3-kinase with Grb-2-associated binding protein-1 and linker for activation of T cells," *J. Thromb. Haemost.*, Nov. 2010, 8(11):2530-2541.
Muntean and Crispino, "Differential requirements for the activation domain and FOG-interaction surface of GATA-1 in megakaryocyte gene expression and development," *Blood*, Apr. 2005, 106(4):1223-1231.
Scotland et al., "C-type natriuretic peptide inhibits leukocyte recruitment and platelet-leukocyte interactions via suppression of P-selectin expression," *Proc Natl Acad Sci USA*, Oct. 2005, 102(40):14452-14457.
Yoder et al., "Reduced ability of C-type natriuretic peptide (CNP) to activate natriuretic peptide receptor B (NPR-B) causes dwarfism in lbab −/− mice," *Peptides*, Sep. 2008, 29(9):1575-1581.

* cited by examiner

*Primary Examiner* — Zachary Howard
(74) *Attorney, Agent, or Firm* — Fish & Richardson P.C.

(57) ABSTRACT

This document relates to methods and materials for treating diseases or disorders associated with elevated platelet counts (e.g., essential thrombocythemia, secondary thrombocytosis, congenital amegakaryocytic thrombocytopenia, sepsis, or asplenism) as well as methods and materials for treating diseases or disorders associated with elevated platelet adhesion to collagen (e.g., acute coronary syndromes, angina pectoris, chronic atherosclerosis, diabetes, or hypertension).

6 Claims, 11 Drawing Sheets

Figure 7
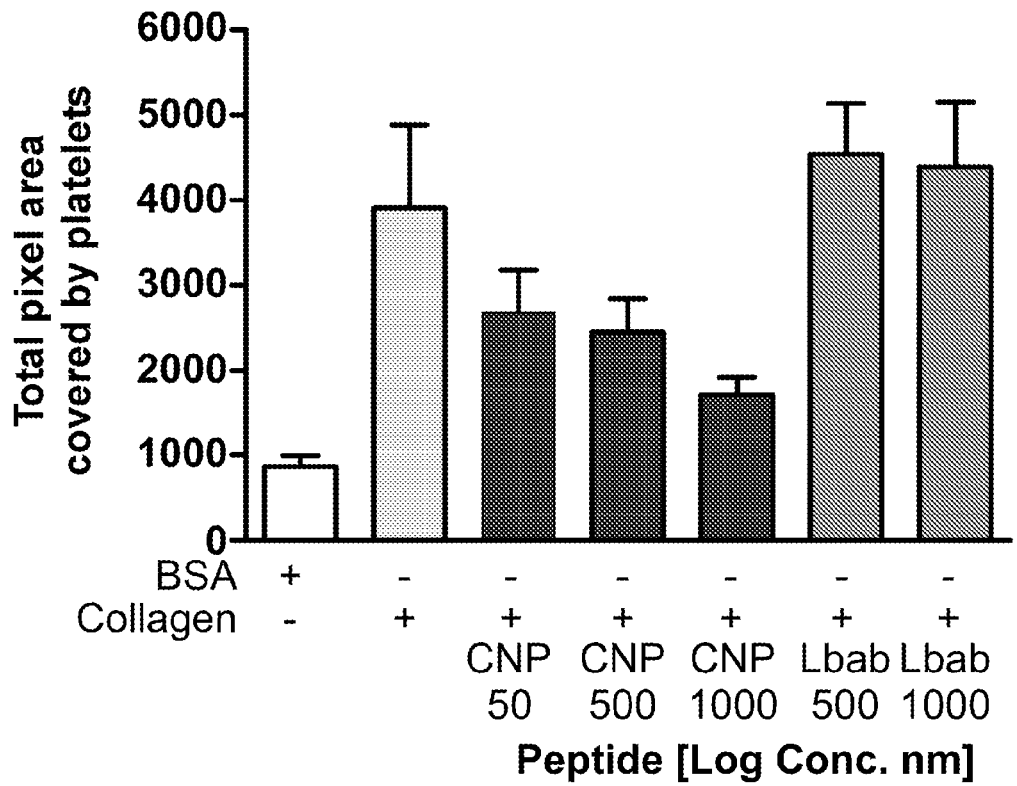
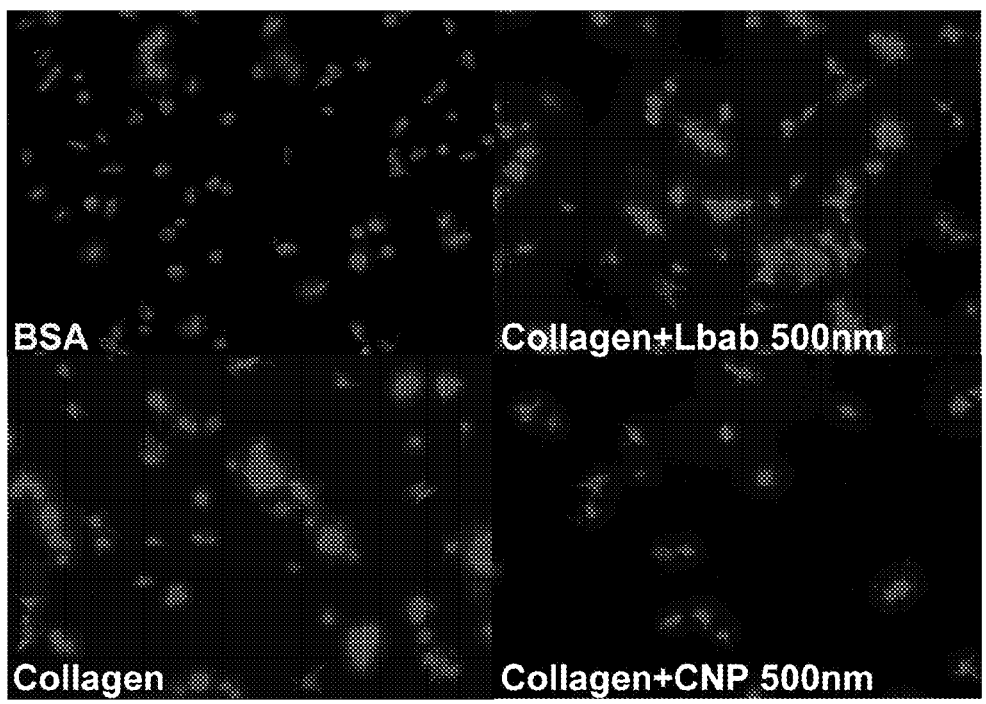

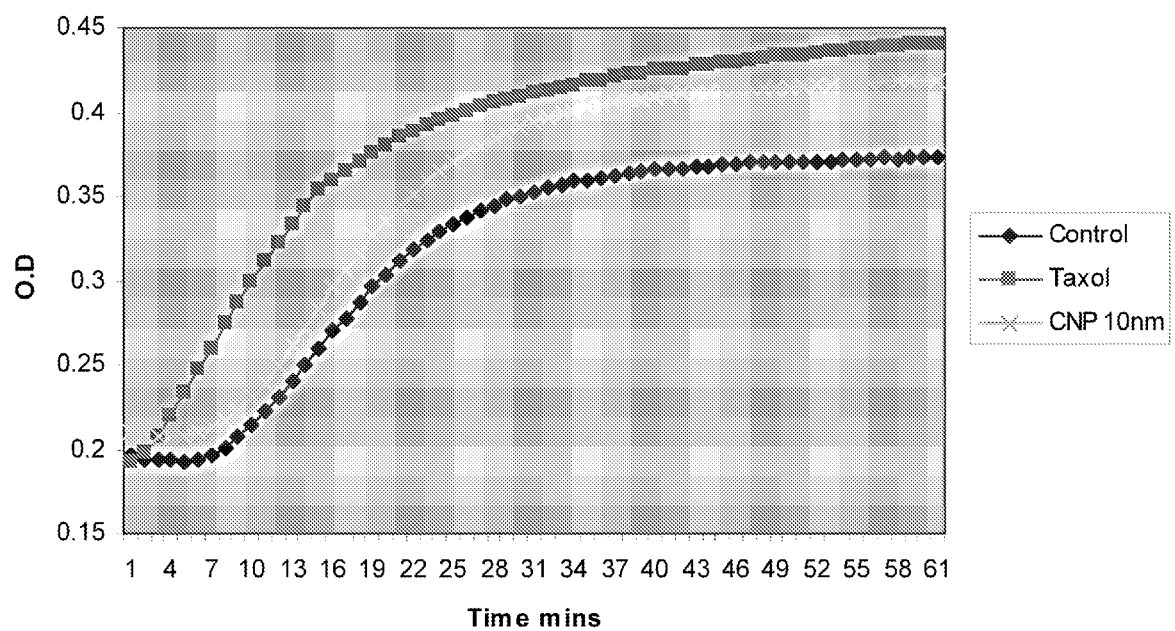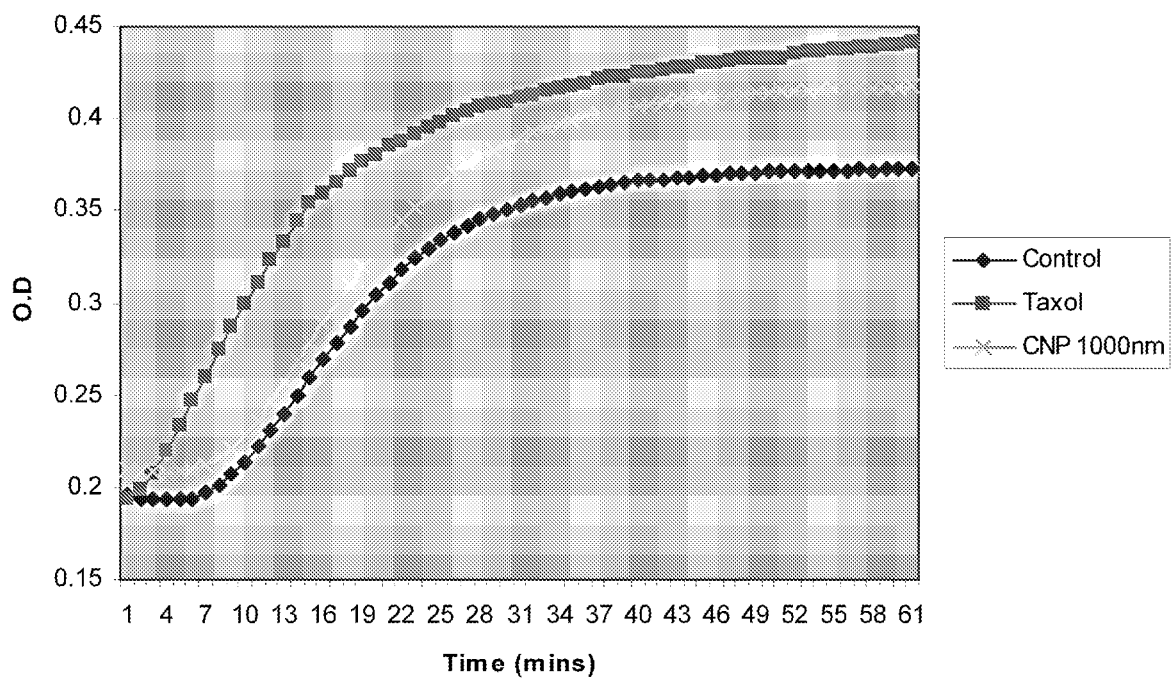
Figure 11

METHODS FOR REDUCING PLATELET COUNTS AND/OR PLATELET ADHESION BY ADMINISTERING A GC-B RECEPTOR AGONIST

CROSS-REFERENCE TO RELATED APPLICATIONS

This application claims the benefit of U.S. Provisional Application Ser. No. 61/437,432, filed Jan. 28, 2011. The disclosure of the prior application is considered part of (and is incorporated by reference in) the disclosure of this application.

STATEMENT AS TO FEDERALLY SPONSORED RESEARCH

This invention was made with government support under grant HL076611 awarded by the National Institutes of Health. The government has certain rights in the invention.

BACKGROUND

1. Technical Field

This document relates to methods and materials for treating diseases or disorders associated with elevated platelet counts (e.g., essential thrombocythemia, secondary thrombocytosis, congenital amegakaryocytic thrombocytopenia, sepsis, or asplenism). This document also relates to methods and materials for treating diseases or disorders associated with elevated platelet adhesion to collagen (e.g., acute coronary syndromes, angina pectoris, chronic atherosclerosis, diabetes, or hypertension).

2. Background Information

The family of natriuretic peptides (NPs) contains three members: atrial natriuretic peptide (ANP), b-type natriuretic peptide (BNP), and c-type natriuretic peptide (CNP). Each of these are cardiovascular-protective in nature and participate in regulatory roles in health and disease. While ANP and BNP are of cardiac origin, CNP is primarily derived from the endothelium as well as bone and brain. The biological actions of NPs are mediated through membrane-bound natriuretic peptide receptors (NPRs). NPR-A (or GC-A) and NPR-B (or GC-B) are guanylyl cyclase linked and activate the cyclic guanosine monophosphate-(cGMP) dependent signaling cascade. ANP and BNP activate GC-A to generate 3', 5' cyclic guanosine monophosphate (cGMP), while CNP activates cGMP through the GC-B receptor.

SUMMARY

This document provides methods and materials for treating diseases or disorders associated with elevated platelet counts (e.g., essential thrombocythemia, secondary thrombocytosis, congenital amegakaryocytic thrombocytopenia, sepsis, or asplenism). For example, this document provides methods and materials for administering CNP or GC-B receptor agonists under conditions that reduce platelet counts within a mammal. As described herein, CNP can bind to GC-B receptors present on megakaryocytes such that cGMP levels increase, megakaryocyte colony formation decreases, the size of megakaryocyte colonies becomes smaller, and platelet counts decrease. Having the ability to reduce platelet counts within a mammal can allow clinicians and patients to treat diseases and disorders associated with elevated platelet counts such as essential thrombocythemia, secondary thrombocytosis, congenital amegakaryocytic thrombocytopenia, sepsis, or asplenism.

This document also provides methods and materials for treating diseases or disorders associated with elevated platelet adhesion (e.g., unstable angina, atherosclerosis, or diabetic or hypertensive states). For example, this document provides methods and materials for administering CNP or GC-B receptor agonists under conditions that reduce platelet adhesion (e.g., platelet adhesion to collagen) within a mammal. As described herein, CNP can bind to GC-B receptors present on platelets such that the level of platelet adhesion to collagen within a mammal decreases. Such a decrease can occur in a cGMP independent manner. Having the ability to reduce platelet adhesion within a mammal can allow clinicians and patients to treat diseases and disorders associated with elevated platelet adhesion such as acute coronary syndromes, angina pectoris, chronic atherosclerosis, diabetes, or hypertension.

In general, one aspect of this document features a method for reducing elevated platelet counts within a mammal. The method comprises, or consists essentially of, administering, to the mammal, a GC-B receptor agonist under conditions wherein the number of platelets within the mammal is reduced. The mammal can be a human. The method can comprise identifying the mammal as having the elevated platelet counts prior to the administering step. The method can comprise assessing the mammal, after the administering step, for a reduction in the number of platelets within the mammal. The GC-B receptor agonist can be a CNP polypeptide. The GC-B receptor agonist can be a human CNP polypeptide.

In another aspect, this document features a method for reducing platelet adhesion within a mammal. The method comprises, or consists essentially of, administering, to the mammal, a GC-B receptor agonist under conditions wherein the level of platelet adhesion within the mammal is reduced. The mammal can be a human. The method can comprise identifying the mammal as having elevated platelet adhesion prior to the administering step. The method can comprise assessing the mammal, after the administering step, for a reduction in the level of platelet adhesion within the mammal. The GC-B receptor agonist can be a CNP polypeptide. The GC-B receptor agonist can be a human CNP polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4 also contains photographs of cells treated with CNP (1000 nM) or the Lbab polypeptide (1000 nM). Treatment with CNP inhibited megakaryocyte colony formation as compared to treatment with the Lbab polypeptide. *=p<0.05 vs. Lbab; **=p<0.01 vs. Lbab.

FIG. 7 contains a graph plotting the total pixel area covered by platelets for platelets treated with the indicated amount of CNP or the Lbab polypeptide. FIG. 7 also contains a photograph of the degree of platelet adhesion to collagen when treated as indicated. CNP (500 nM) inhibited platelet adhesion to collagen. *=p<0.05 vs. platelets treated with 500 nM of the Lbab polypeptide.

FIGS. 11A and 11B are graphs plotting tubulin polymerization. CNP induced tubulin polymerization at the indicated concentrations in an assay that measures direct tubulin polymerization. Taxol is a known potent agent that stabilizes microtubules. O.D. reflects tubulin polymerization.

DETAILED DESCRIPTION

This document provides methods and materials for treating diseases or disorders associated with elevated platelet counts (e.g., essential thrombocythemia, secondary thrombocytosis, congenital amegakaryocytic thrombocytopenia, sepsis, or asplenism). For example, this document provides methods and materials for administering CNP or GC-B receptor agonists under conditions that reduce platelet counts within a mammal. This document also provides methods and materials for treating diseases or disorders associated with elevated platelet adhesion (e.g., unstable angina, atherosclerosis, or diabetic or hypertensive states). For example, this document provides methods and materials for administering CNP or GC-B receptor agonists under conditions that reduce platelet adhesion (e.g., platelet adhesion to collagen) within a mammal.

Figure 2:
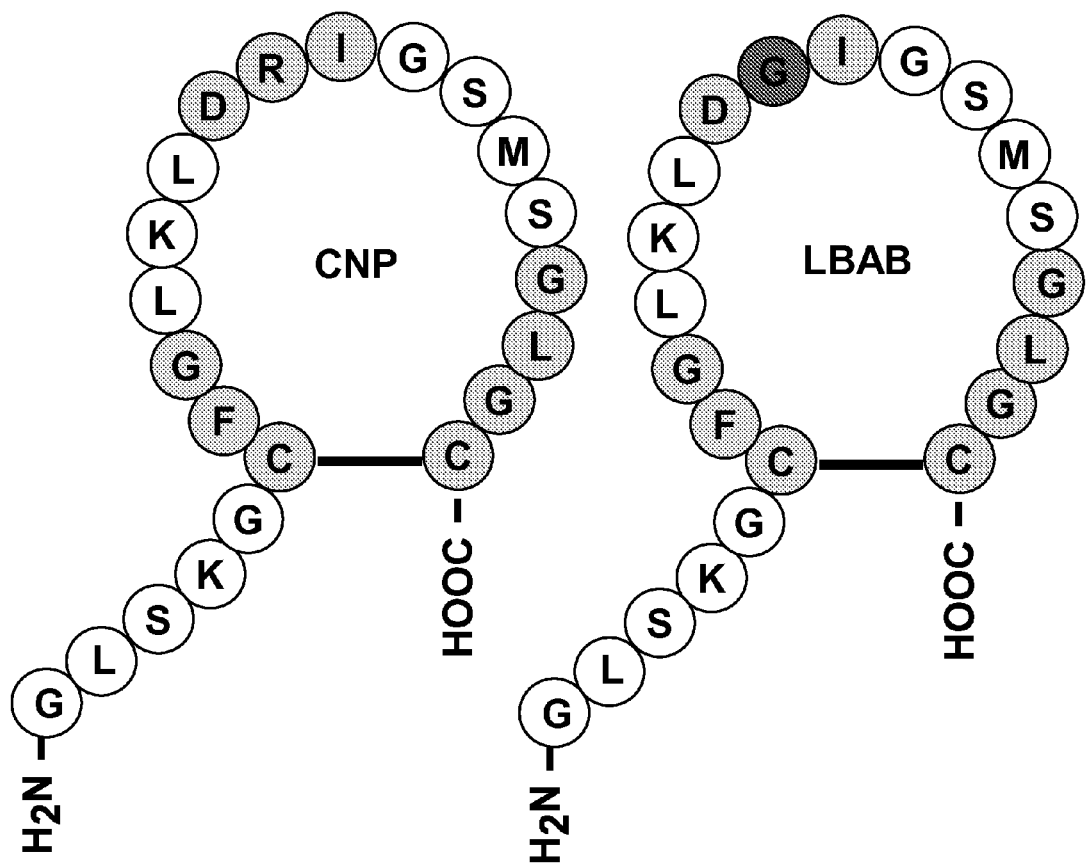
FIG. 2 is a schematic depicting the amino acid sequence of a CNP polypeptide (SEQ ID NO:1) and the Lbab polypeptide (SEQ ID NO:2). The lightly shaded residues indicate conserved natriuretic polypeptide residues of CNP, and the darker shaded residue indicates the Arg to Gly substitution of the Lbab polypeptide.

The mammal can be any type of mammal including, without limitation, a mouse, rat, dog, cat, horse, sheep, goat, cow, pig, monkey, or human. For example, a mammal such as a human with thrombocytosis can be treated by administering a CNP polypeptide, a GC-B receptor agonist, or a combination thereof under conditions that reduce platelet counts within that human. In the cases of humans, a CNP polypeptide can have the amino acid sequence set forth in FIG. 2. Other examples of CNP polypeptides include, without limitation, preproCNP polypeptides (GenBank GI No. 13249346, Accession No. NP077720.1) and chimeras made with a CNP polypeptide including CD-NP as described elsewhere (Lisy et al., *J. Am. Coll. Cardiol.*, 52:60-68 (2008)). Examples of GC-B receptor agonists include, without limitation, CNP polypeptides, ANP polypeptides, and BNP polypeptides.

A polypeptide provide herein can be obtained by chemical synthesis (e.g., using solid phase polypeptide synthesis methods or an peptide synthesizer such as an ABI 431A Peptide Synthesizer; Applied Biosystems; Foster City, Calif.) or by expression of a recombinant nucleic acid encoding the polypeptide. For example, standard recombinant technology using expression vectors encoding a polypeptide provide herein can be used. The resulting polypeptides then can be purified using, for example, affinity chromatographic techniques and HPLC. The extent of purification can be measured by any appropriate method including, without limitation, column chromatography, polyacrylamide gel electrophoresis, and high-performance liquid chromatography. A polypeptide provide herein can be designed or engineered to contain a tag sequence that allows the polypeptide to be purified (e.g., captured onto an affinity matrix). For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

A polypeptide provided herein (e.g., a human CNP polypeptide) can be formulated as a pharmaceutical composition by admixture with pharmaceutically acceptable non-toxic excipients or carriers. Such compositions can be administered to a mammal in need thereof in an amount effective to treat, for example, a disease or disorder associated with elevated platelet counts or a disease or disorder associated with elevated platelet adhesion. Any appropriate route of administration can be used to administer a CNP polypeptide, a GC-B receptor agonist, or a combination thereof to a mammal having a disease or disorder associated with elevated platelet counts or a disease or disorder associated with elevated platelet adhesion. For example, oral, intravenous, intramuscular, subcutaneous, sublingual, or intracardiac routes of administration can be used.

In some cases, a CNP polypeptide can be used in combination with one or more other GC-B receptor agonists to treat a disease or disorder associated with elevated platelet counts or to treat a disease or disorder associated with elevated platelet adhesion. For example, a human CNP polypeptide can be used in combination with a human ANP polypeptide or a human BNP polypeptide to treat a disease or disorder associated with elevated platelet counts or to treat a disease or disorder associated with elevated platelet adhesion.

Prior to treatment, a mammal (e.g., human) to be treated can be identified as having a disease or disorder associated with elevated platelet counts or a disease or disorder associated with elevated platelet adhesion using standard clinical techniques. For example, a Coulter counter can be used to determine whether or not a human has thrombocytosis. Once identified as having a disease or disorder associated with elevated platelet counts or a disease or disorder associated with elevated platelet adhesion, a composition containing a CNP polypeptide, a GC-B receptor agonist, or a combination thereof can be administered to the mammal in any amount, at any frequency, and for any duration effective to achieve a desired outcome (e.g., to reduce platelet counts or to reduce platelet adhesion). In some cases, a composition containing a CNP polypeptide, a GC-B receptor agonist, or a combination thereof can be administered to a mammal to reduce platelet counts or platelet adhesion in the mammal by 5, 10, 15, 20, 25, 30, 35, 40, 45, 50, 55, 60, 65, 70 percent or more). An effective amount of a CNP polypeptide or a GC-B receptor agonist can be any amount that reduces platelet counts or platelet adhesion without producing significant toxicity to the mammal. Typically, an effective amount of a CNP polypeptide or a GC-B receptor agonist can be any amount greater than or equal to about 0.01 µg/kg provided that that amount does not induce significant toxicity to the mammal upon administration. In some cases, an effective amount of a CNP polypeptide or a GC-B receptor agonist can be between about 0.01 µg/kg and about 10 mg/kg (e.g., between about 0.01 µg/kg and about 5 mg/kg, between about 0.01 µg/kg and about 2.5 mg/kg, between about 0.01 µg/kg and about 1 mg/kg, between about 0.01 µg/kg and about 0.5 mg/kg, between about 0.1 µg/kg and about 10 mg/kg, between about 0.5 µg/kg and about 10 mg/kg, or between about 1 µg/kg and about 10 mg/kg). Various factors can influence the actual effective amount used for a particular application. For example, the frequency of administration, duration of treatment, use of multiple treatment agents, route of administration, and severity of the disease or disorder may require an increase or decrease in the actual effective amount administered.

The frequency of administration of a CNP polypeptide or a GC-B receptor agonist can be any frequency that reduces platelet counts or platelet adhesion without producing significant toxicity to the mammal. For example, the frequency of administration can be from about once a week to about once a month. The frequency of administration can remain constant or can be variable during the duration of treatment. For example, a CNP polypeptide or a GC-B receptor agonist can be administered daily, twice a day, five days a week, or three days a week. A CNP polypeptide or a GC-B receptor agonist can be administered for five days, 10 days, three weeks, four weeks, eight weeks, 48 weeks, one year, 18 months, two years, three years, or five years. A course of treatment can include rest periods. For example, a CNP polypeptide or a GC-B receptor agonist can be administered for five days followed by a ten-day rest period, and such a regimen can be repeated multiple times. As with the effective amount, various factors can influence the actual frequency of administration used for a particular application. For example, the effective amount, duration of treatment, use of multiple treatment agents, route of administration, and severity of the disease or disorder may require an increase or decrease in administration frequency.

An effective duration for administering a CNP polypeptide or a GC-B receptor agonist can be any duration that reduces platelet counts or platelet adhesion without producing significant toxicity to the mammal. Thus, the effective duration can vary from several days to several weeks, months, or years. In general, the effective duration for the treatment of a disease or disorder associated with elevated platelet counts or a disease or disorder associated with elevated platelet adhesion can range in duration from several days to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the disease or disorder.

The invention will be further described in the following examples, which do not limit the scope of the invention described in the claims.

EXAMPLES

Example 1

Mouse Megakaryocytes Express GC-B

Primary hematopoietic progenitor cells were isolated from mouse fetal livers of E13.5 embryos (C57B1/6) or from femurs and tibias of C57B1/6 mice using the EasySep negative selection mouse hematopoietic progenitor enrichment kit (Stem Cell Technologies, Vancouver, BC). The progenitor cells were then expanded for two days in serum free expansion media containing 50% RPMI using standard techniques to generate megakaryocytes (Huang et al., *J. Clin. Invest.*, 117(12):3890-9 (2007) and Muntean and Crispino, *Blood*, 106(4):1223-31 (2005)). The purity of the megakaryocytes was assessed using acetylcholinesterase (AchE) staining using standard protocols and FACS with CD41 (Emfret Analytics).

Figure 1:
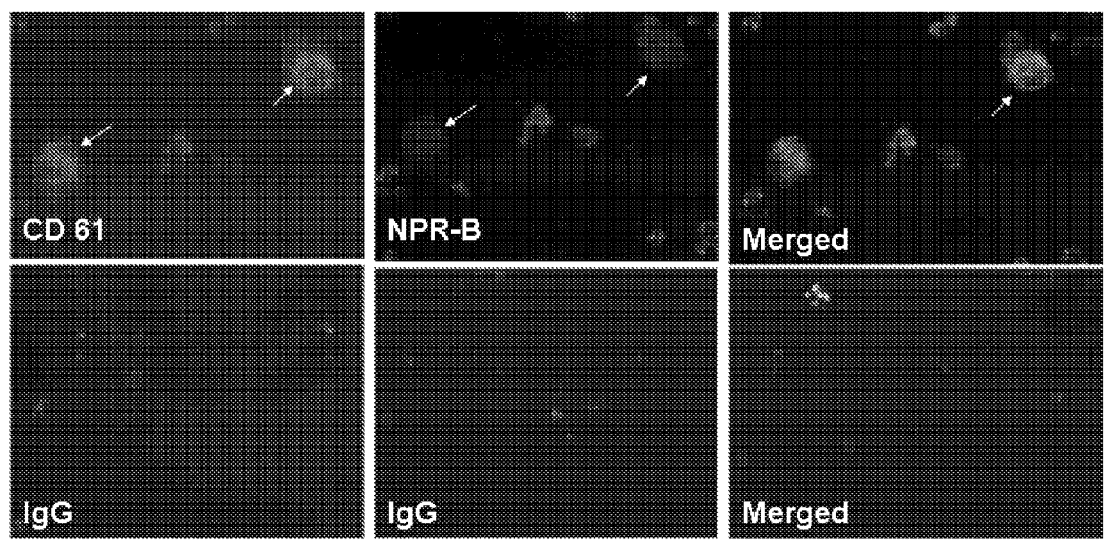
FIG. 1 is a photograph of immunostaining results demonstrating the co-localization of CD61 and GC-B in murine megakaryocytes.

Once obtained, the megakaryocytes were spun down in a cytospin to obtain slides for immunostaining. The slides were fixed and blocked with 10% normal goat serum and incubated with rabbit anti-GC-B (4 ng/mL; Santa Cruz Biotechnology, INC., Santa Cruz, Calif.) and Alexa Fluor 488 anti-mouse/rat CD61 (10 µg/mL; Biolegend, San Diego, Calif.) in PBS. Goat anti-rabbit Texas Red 1:500 (Molecular Probes, Eugene, Oreg.) were used to visualize the rabbit anti-GC-B. Matched IgG negative controls also were used. The immunostaining revealed that megakaryocytes express GC-B, the receptor for CNP. GC-B and CD61 were colocalized on mouse megakaryocytes (FIG. 1).

Example 2

CNP Stimulates cGMP Production in Megakaryocytes

The following was performed to determine if GC-B present on megakaryocytes is functional and responsive to CNP. Megakaryocytes were treated with either CNP or a single residue mutant CNP designated Lbab for 30 minutes at 37° C. with 5% $CO_2$ in IMDM media supplemented with 1% Nutridoma, penicillin, streptomycin, L-glutamine, and recombinant TPO. The Lbab polypeptide (FIG. 2) is described elsewhere (Yoder et al., *Peptides*, 29(9):1575-81 (2008)).

Figure 3:
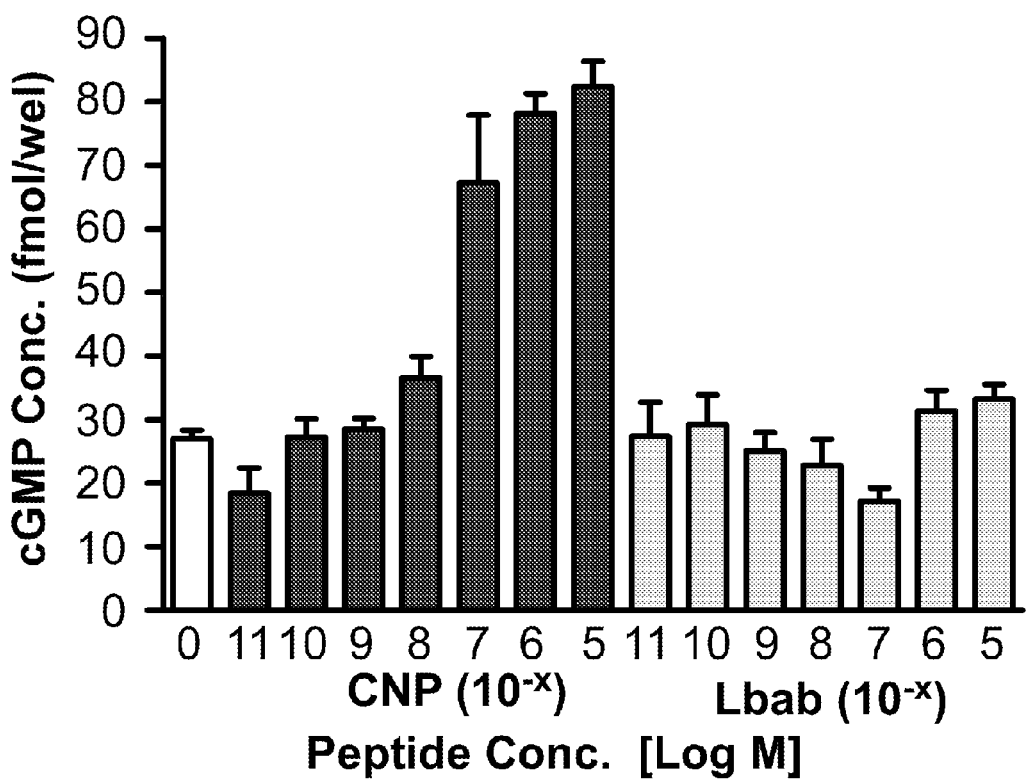
FIG. 3 is a graph plotting the level (fmol/well) of cGMP production by megakaryocytes exposed to the indicated amount of CNP or Lbab polypeptides. Exposure to CNP, but not the Lbab polypeptide, stimulated cGMP production in megakaryocytes. *=p<0.05 vs. cells treated with the Lbab polypeptide.

After the incubation, the cells were lysed, and the amount of cGMP was measured using a BIOTRAK cGMP enzyme immunoassay system Kit (GE Healthcare Bio-Sciences Corp.). CNP stimulated a dose-dependent increase in cGMP formation as compared with the levels of stimulation observed in cells exposed to the Lbab polypeptide (FIG. 3).

Example 3

CNP Inhibits Colony Formation in Megakaryocytes

Figure 4:
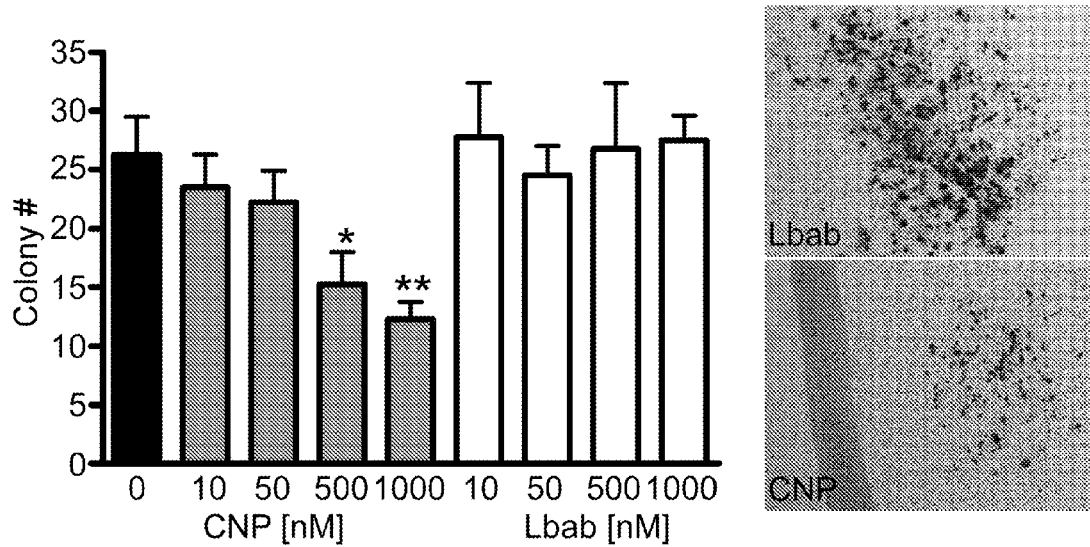
FIG. 4 contains a graph plotting the number of colonies formed for cells treated with the indicated amount of CNP or the Lbab polypeptide.

To determine the effect of CNP on the colony forming ability of megakaryocytes, colony formation assays were conducted using MegaCult®-C (StemCell Tech) as per the manufacturer's protocol. Mice were euthanized, and bone marrow was collected from femurs and tibias by flushing the bones multiple times with IMDM. Once a single cell suspension was achieved, the cells were added to MegaCult®-C medium containing cytokines and collagen. The cell suspension was then dispensed into the chamber slide at the concentration of 20,000 cells/well and incubated at 37° C. with 5% $CO_2$ and >95% humidity for 6 to 8 days. The cells were then dehydrated and fixed with acetone followed by acetylcholinesterase staining. The colonies were scored using a 5× objective, and 10× objective was used to examine colonies in greater detail. Mouse megakaryocytes and early megakaryocyte progenitors expressed acetylcholinesterase and exhibited brown granular deposits unlike non-megakaryocyte colonies that lack the brown precipitates. CNP not only inhibited colony formation, but significantly affected colony size (FIG. 4).

Example 4

Mouse and Human Platelets Express GC-B

Within an hour of platelet pheresis, human platelets were collected by centrifugation at 2,300×g for 10 minutes. Once spun, the pellet was washed two times with wash buffer containing an anticoagulant, a thrombin inhibitor, and two platelet antagonists. After a final wash, the pellet containing the platelets was lysed on ice for 10 minutes. The sample then was centrifuged, and the supernatant was collected. Increasing amounts of protein (FIG. 5, top panel) were used for SDS-PAGE, and GC-B expression was detected using an anti-GC-B antibody. Actin was detected as a control using an anti-actin antibody (Santa Cruz Biotech).

Figure 5:
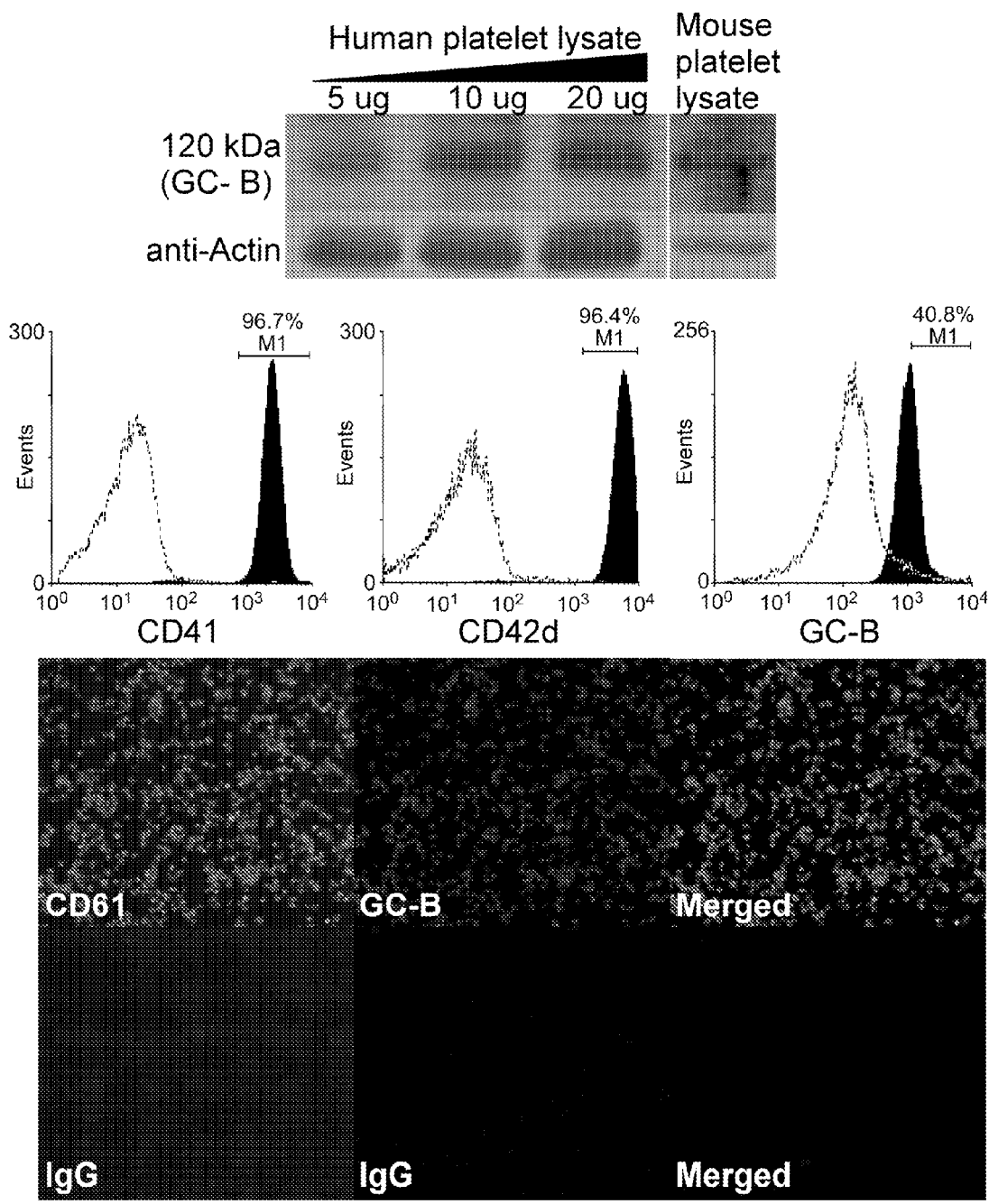
FIG. 5 contains photographs and graphs demonstrating that mouse and human platelets express GC-B.

Platelet isolation was adapted from studies described elsewhere (Boylan et al., *Blood*, 108(3):908-14 (2006); Moraes et al., *J. Thromb. Haemost.*, 8(11):2530-41 (2010); and Bougie et al., *Blood*, 116(16):3033-8 (2010)). Briefly, C57BL/6 mice were anesthetized with ketamine/xylazine. Blood was obtained from the vena cava and collected into 3.8% sodium citrate. The whole blood was then diluted with equal volumes of Tyrode's buffer containing $PGE_1$ (50 ng/mL), glucose (1 mg/mL), and BSA (2.5 mg/mL) before being spun at 280×g to obtain platelet rich plasma (PRP). The upper $314^{th}$ of the PRP was collected and spun for 10 minutes to collect the platelets. The platelets were then washed with Tyrode's buffer before any analysis was performed. The platelets were counted, visualized by microscopy, and then used for FACS analysis, immunostaining, and western blotting. CD41, CD42D, and GC-B expression was detected by FACS (FIG. 5, middle panel).

The PRP was spun down in a cytospin at 1000 rpm for 3 minutes to obtain slides of mouse platelets. These slides were fixed and blocked with 10% normal goat serum and incubated with rabbit anti-GC-B (4 µg/mL; Santa Cruz Biotechnology, INC., Santa Cruz, Calif.) and an Alexa Fluor 488 anti-mouse, rat CD61 antibody (10 µg/mL; Biolegend) in PBS. Goat anti-rabbit Texas Red 1:500 (Molecular Probes) was used to visualize the rabbit anti-GC-B. Matched IgG negative controls were also used. CD61 and GC-B expression colocalized in mouse platelets (FIG. 5, bottom panel).

Example 5

CNP does not Alter cGMP Production in Platelets

Figure 6:
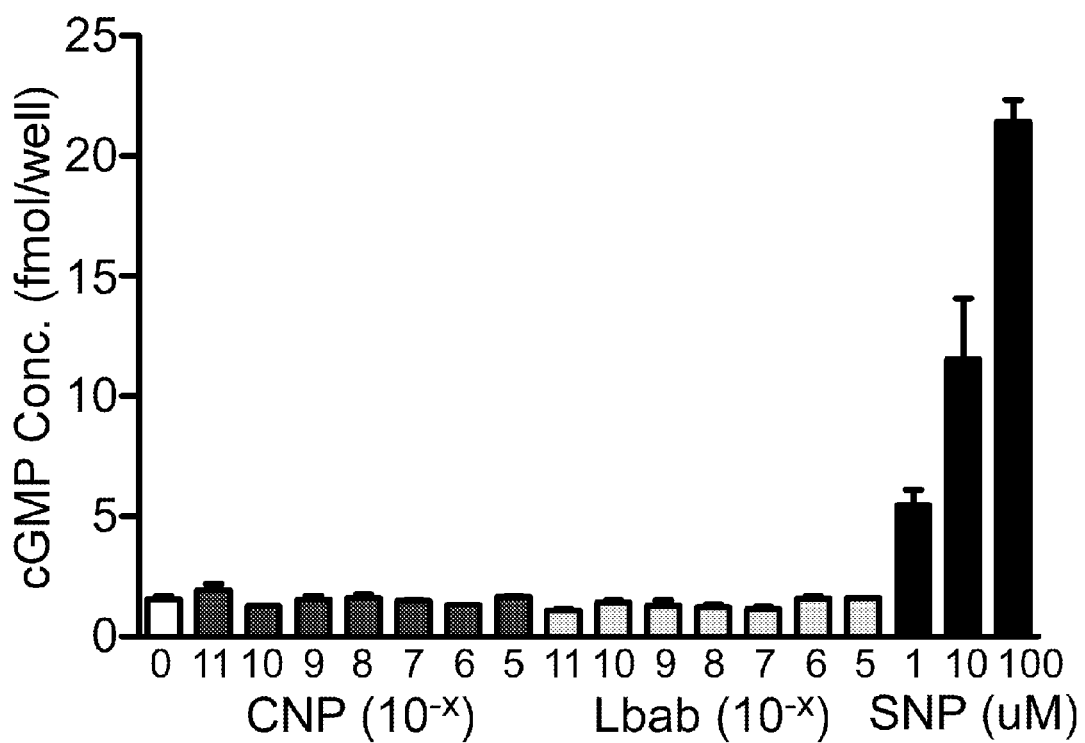
FIG. 6 is a graph plotting the level (fmol/well) of cGMP production by mouse platelets exposed to the indicated amount of CNP, the Lbab polypeptide, or sodium nitroprusside (SNP).

The effect of CNP on cGMP production in platelets was studied. Washed platelets were treated with CNP or the mutant Lbab polypeptide for 30 minutes at 37° C. with 5% $CO_2$ in Tyrode's buffer with 1 mM $Ca^{+2}$. After the incubation, the cells were lysed, and the amount of cGMP was calculated according to the standard curve that was generated from parallel reactions within the same experiment. Interestingly, while the nitric oxide donor sodium nitroprusside (SNP) increased cGMP production in platelets, CNP did not affect cGMP levels (FIG. 6). These results indicate that any effects of CNP on platelets could be independent of cGMP generation.

Example 6

CNP Inhibits Platelet Adhesion on Collagen

The role of CNP on platelet aggregation and platelet adhesion to fibrinogen, fibronectin, and collagen were assessed. Human platelets or platelets from C57B1/6 mice were isolated and treated with either CNP or the Lbab polypeptide for 30 minutes at 37° C. with 5% $CO_2$. Following treatment, the platelets were gently added to cover slips pre-blocked with 1% BSA and pre-coated with fibrinogen, fibronectin, or collagen (50 µg/mL, CHRONOLOG Corp., Havertown, Pa.). $Ca^{+2}$ and $Mg^{+2}$ were added to 1 mM and 2 mM, respectively, before incubation at 37° C. for 30 minutes. The platelets were then fixed and permeabilized before staining with TRITC Phalloidin (0.5 µg/mL; Sigma) for an hour. The platelets were then gently washed a couple of times with PBS and mounted in Vectashield mounting medium (Vector laboratories, Burlingame, Calif.) and sealed with nail polish as described elsewhere (Moraes et al., *J. Thromb. Haemost.*, 8(11):2530-41 (2010); and Bougie et al., Blood, 116(16):3033-8 (2010)). Images were acquired from five consecutive fields using a Zeiss Axioscop microscope (Carl Zeiss, Oberkochen, Germany) with a Zeiss 100× oil-immersion lens. The images were analyzed using ImageJ software.

Figure 8:
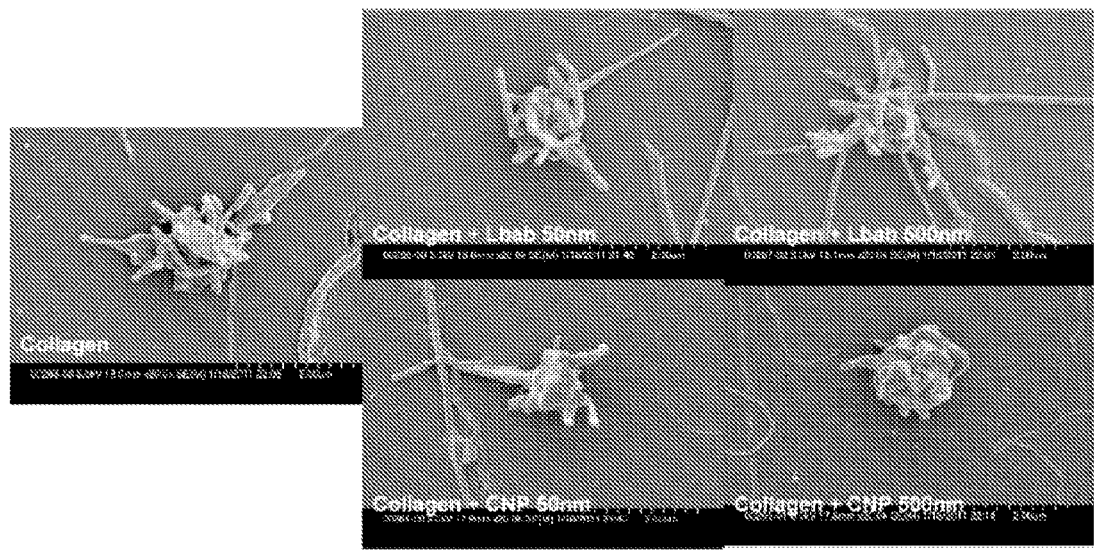
FIG. 8 contains photographs of platelets in the presence of collagen and treated with the indicated amount of CNP or the Lbab polypeptide. Platelets treated with varying concentrations of CNP have aberrant filopodia (bottom row) compared to those treated with the Lbab polypeptide.

These studies demonstrated that platelet aggregation was unaffected in the presence of CNP (data not shown). The results of these experiments revealed that there was no significant difference in the adhesion of Lbab polypeptide-treated or CNP-treated platelets to fibrinogen and fibronectin. As evident from FIG. 7, CNP attenuated platelet adhesion to collagen when compared to the control polypeptide. While Lbab treated platelets exhibited near normal platelet adhesion to collagen and had normal sprouting of pseudopodia; platelets treated with CNP had significantly decreased number of platelets adhered to collagen 2451±39 for CNP vs. 4536±43 for Lbab at 500 nM and 1712±20 for CNP vs. 4390±24 for Lbab at 1000 nM; P<0.05; n=5 and importantly, the vast majority of adhered platelets had abnormal pseudopodia formation. These findings also were confirmed by electron microscopy (FIG. 8). These results demonstrate that CNP attenuates platelet adhesion to collagen and that CNP might have effects on platelet cytoskeleton.

The results provided herein demonstrate that megakaryocytes and platelets express GC-B. These results also demonstrate that CNP is capable of stimulating cGMP in megakaryocytes and is capable of inhibiting megakaryocyte colony formation. CNP does not stimulate cGMP in platelets, but is capable of inhibiting collagen-mediated platelet adhesion. Taken together, these results demonstrate that CNP may mediate megakaryocyte function in a GC-B/cGMP-dependent manner, while CNP may affect platelet adhesion independent of cGMP.

Example 7

Effects of CNP on Cytoskeletal Proteins Tubulin and Actin

Figure 9:
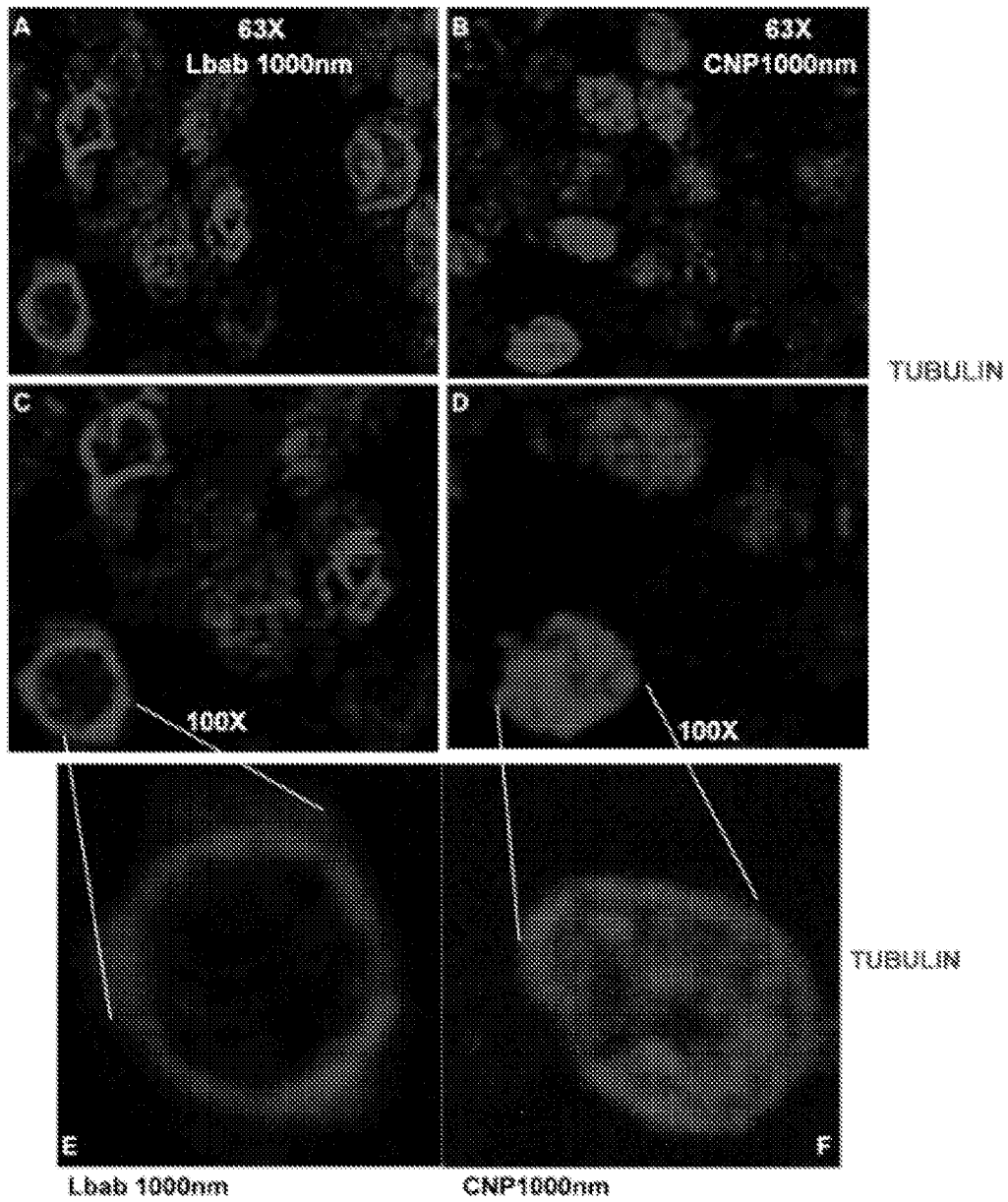
FIG. 9 contains photographs of platelets treated with the Lbab polypeptide, which exhibit stable tubulin polymerization (A, C, E), and platelets treated with CNP, which exhibit destabilized tubulin (B, D, F).
Figure 10:
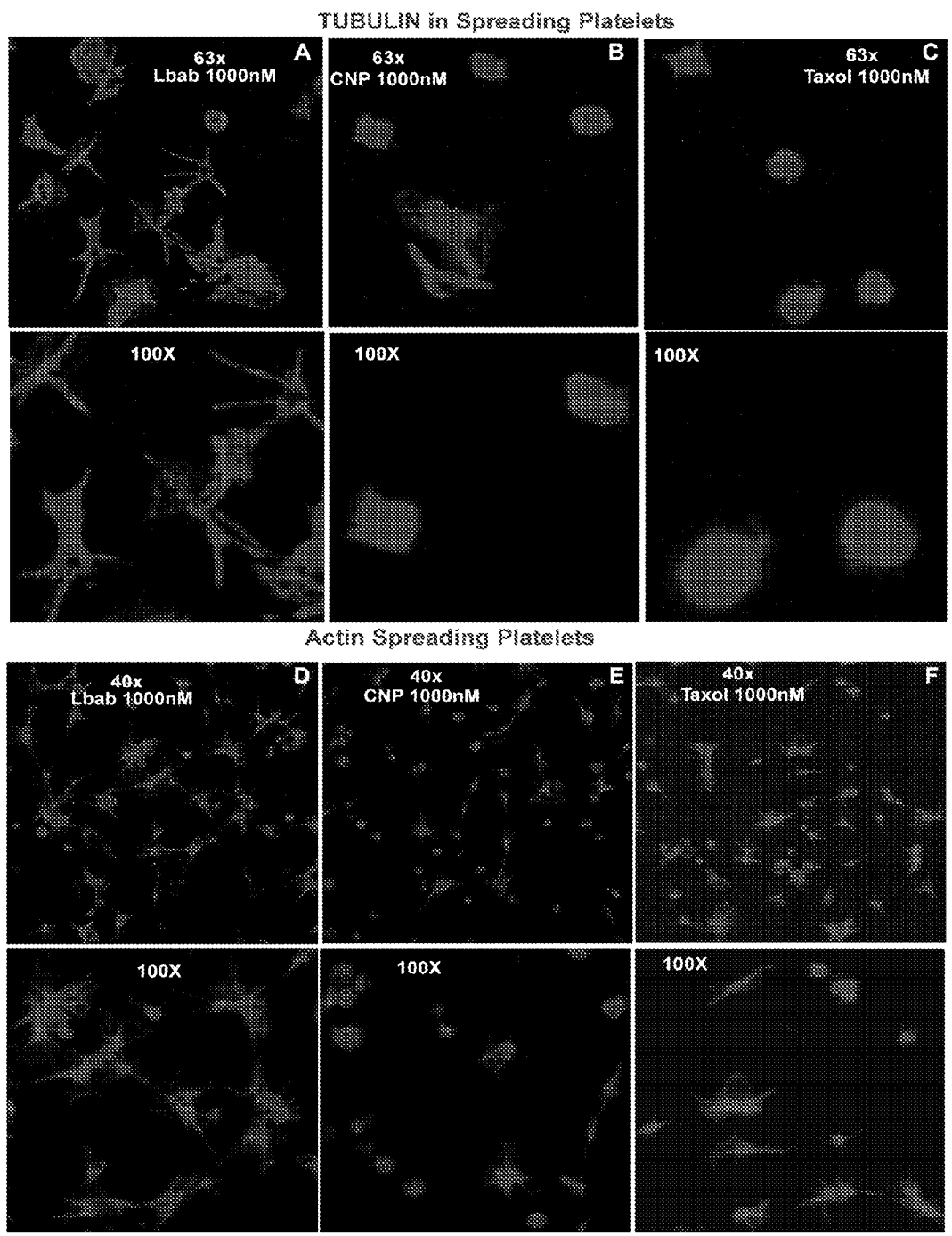
FIG. 10 contains photographs of platelets treated with the indicated amount of the Lbab polypeptide, CNP, or taxol. CNP inhibits tubulin distribution in spreading platelets (column B) similar to taxol (column C), and Lbab does not demonstrate such an affect (column A). In distinction, CNP and taxol have minimal effect on actin distribution in spreading platelets (column E and F) compared to platelets treated with the Lbab polypeptide (column D).

The following was performed to determine if CNP could affect cytoskeletal proteins such as tubulin and/or actin. To delineate this function of CNP, human platelets were either treated with the Lbab polypeptide or CNP and were placed on slides using cytospin Immunocytochemistry was performed with anti-tubulin or anti-actin antibodies. Platelets treated with the control Lbab polypeptide were capable of forming clear marginal bands within platelets (FIG. 9). In contrast, platelets treated with CNP had decreased marginal band formation (FIG. 9). These results indicate that CNP affects the dynamic process of tubulin polymerization and depolymerization. In distinction to CNP's effects on tubulin, these results demonstrate that CNP does not influence actin function significantly (FIG. 10).

To confirm these findings, tubulin and actin also were stained on platelets that were viable and functionally active using a spreading assay. In addition, within these experiments, Taxol, a compound known to stabilize microtubules, was used as a positive control and interestingly, CNP mirrored the effects of Taxol (FIG. 10).

Example 8

CNP has a Direct Effect on Tubulin Polymerization

To demarcate whether the effects of CNP on microtubules was direct or indirect, a microtubule polymerization assay from cytoskeleton was utilized as per manufacturer's protocol. The assay studied all three phases of microtubule formation, namely nucleation, growth, and steady state equilibrium. The results of the experiment revealed that CNP, analogous to Taxol, has effects on the growth and steady state phases of tubulin polymerization (FIG. 11).

Example 9

Methods and Materials

Platelet Aggregation and Secretion

Platelet aggregation was performed at 37° C. in lumi-aggregometer in the presence of luciferin-luciferase to simultaneously measure light transmission and secretion of dense granule-derived ATP. Basically, 10 μL of Chronolume (Chrono-Log, Havertown, Pa.) and platelets at ($3.0 \times 10^8$ platelets/mL) were added to siliconized glass cuvettes at 37° C. with constant stirring. $CaCl_2$ was added to a final concentration of 1 mM. Platelet aggregation and secretion was measured in a lumi-aggregometer (Chrono-Log, Havertown, Pa.) for 1 minute following which the polypeptide (CNP or Lbab) was added to the platelets, and aggregation and secretion were measured once again for 2 minutes in order to determine if the polypeptide itself activates the platelets. Finally, thrombin was added (up to 1 U/mL) as was collagen (up to 10 μg/mL) and collagen-related polypeptide (CRP up to 10 μg/mL, or ADP up to 10 μM) to activate the platelets. Aggregation and secretion were measured for 15 minutes.

Platelet Adhesion Assay

Platelets were isolated and treated with either CNP or the mutant Lbab polypeptide for 30 minutes at 37° C. with 5% $CO_2$. Following treatment, the platelets were gently added to cover slips pre-blocked with 1% BSA and pre-coated with collagen (50 mg/mL, CHRONOLOG-corporation). $Ca^{+2}$ and $Mg^{+2}$ were added to 1 mM and 2 mM, respectively, before incubation at 37° C. for 30 minutes. The platelets were then fixed and permeabilized before staining with TRITC Phalloidin (0.5 μg/mL; Sigma) for an hour. The platelets were then gently washed a couple of times with PBS and then mounted in Vectashield mounting medium (Vector laboratories, Burlingame, Calif.) and sealed with nail polish. Images were acquired from five consecutive fields using Zeiss Axioscop microscope (Carl Zeiss, Oberkochen, Germany) with a Zeiss 100× oil-immersion lens and analyzed using ImageJ software.

Electron Microscopy

Cells were placed in Trump's fixative, 4% formaldehyde: 1% glutaraldehyde for 1 hour or longer at 4° C. After two rinses in 0.1 M sodium phosphate buffer (pH 7.2), samples were dehydrated in a graded ethanol series to 100% ethanol at which time they were critical point dried with liquid carbon dioxide. They were then mounted on specimen stubs, sputter-coated with gold-palladium, and examined with a Hitachi S4700 scanning electron microscope.

Immunocytochemistry

PRP was spun down in a cytospin at 1000 rpm for 2 minutes to obtain slides of mouse/human platelets. These slides were fixed and blocked with 10% normal goat serum and incubated with mouse anti-tubulin antibody at 1:700 (Sigma) in PBS. Goat anti-mouse Alexa Fluor 594 at 1:500 (Molecular Probes) was used to visualize the tubulin. Matched negative controls also were used.

Tubulin Polymerization Assay

A 96-well plate was warmed in the incubator to 37° C. for 10 minutes. During this time, 10× stock solutions of compounds to be tested were prepared. 5 μL of control buffer, 5 μL of the 10× paclitaxel stock, and 5 μL of the 10× test compound were added to their respective wells. Next, the 96 well plate was placed back into warm plate reader for 1 minute. Finally, 50 μL of the tubulin reaction mix was added to each of the wells as quickly as possible, and the plate reader was started.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing elevated platelet counts within a mammal, wherein said method comprises:
   (a) identifying said mammal as having elevated platelet counts, and
   (b) administering, to said mammal, a C-type natriuretic peptide (CNP) polypeptide having the amino acid sequence set forth in SEQ ID NO:1 under conditions wherein the number of platelets within said mammal is reduced.

2. The method of claim 1, wherein said mammal is a human.

3. The method of claim 1, wherein said method comprises assessing said mammal, after said administering step, for a reduction in the number of platelets within said mammal.

4. A method for reducing platelet adhesion to collagen within a mammal, wherein said method comprises:
   (a) identifying said mammal as having elevated platelet adhesion to collagen, and
   (b) administering, to said mammal, a C-type natriuretic peptide (CNP) polypeptide having the amino acid sequence set forth in SEQ ID NO:1 under conditions wherein the level of platelet adhesion to collagen within said mammal is reduced.

5. The method of claim 4, wherein said mammal is a human.

6. The method of claim 4, wherein said method comprises assessing said mammal, after said administering step, for a reduction in the level of platelet adhesion to collagen within said mammal.

* * * * *

SEQUENCE LISTING

<160> NUMBER OF SEQ ID NOS: 2

<210> SEQ ID NO 1
<211> LENGTH: 22
<212> TYPE: PRT

```
-continued

<213> ORGANISM: Homo sapiens

<400> SEQUENCE: 1

Gly Leu Ser Lys Gly Cys Phe Gly Leu Lys Leu Asp Arg Ile Gly Ser
 1               5                  10                  15

Met Ser Gly Leu Gly Cys
            20

<210> SEQ ID NO 2
<211> LENGTH: 22
<212> TYPE: PRT
<213> ORGANISM: Homo sapiens
<220> FEATURE:
<223> OTHER INFORMATION: Mutant CNP

<400> SEQUENCE: 2

Gly Leu Ser Lys Gly Cys Phe Gly Leu Lys Leu Asp Gly Ile Gly Ser
 1               5                  10                  15

Met Ser Gly Leu Gly Cys
            20
```